(12) United States Patent
Tom-Moy et al.

(10) Patent No.: US 9,234,892 B2
(45) Date of Patent: Jan. 12, 2016

(54) MULTIPLE EPITOPE DETECTION IN AN FFPE TISSUE SECTION

(71) Applicant: Agilent Technologies, Inc., Loveland, CO (US)

(72) Inventors: May Tom-Moy, Santa Clara, CA (US); Nazumi Alice Yamada, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 65 days.

(21) Appl. No.: 14/273,320

(22) Filed: May 8, 2014

(65) Prior Publication Data

US 2015/0323532 A1 Nov. 12, 2015

(51) Int. Cl.
*G01N 31/00* (2006.01)
*G01N 33/53* (2006.01)
*G01N 33/569* (2006.01)

(52) U.S. Cl.
CPC ................................. *G01N 33/56966* (2013.01)

(58) Field of Classification Search
CPC ................ G01N 2021/7786; C07K 2317/565; C07K 236/96; A61K 2039/5051
See application file for complete search history.

(56) References Cited

PUBLICATIONS

Gerdes, et al., "Highly multiplexed single-cell analysis of formalinfixed, paraffin-embedded cancer tissue", Proceedings of the National Academy of Sciences, vol. 110, issue 29, pp. 11982-11987.
Giesen, et al., "Highly multiplexed imaging of tumor tissues with subcellular resolution by mass cytometry", nature methods, vol. 11, No. 4, 2014, pp. 417-425.
Glass, et al., "SIMPLE: A Sequential Immunoperoxidase Labeling and Erasing Method", Journal of Histochemistry & Cytochemistry, vol. 57(10): 899-905, 2009.
Tramu, et al. "An efficient method of antibody elution for the successive or simultaneous localization of two antigens by immunocytochemistry", J Histochem Cytochem. Apr. 1978;26(4):322-4.

*Primary Examiner* — Lisa Cook

(57) ABSTRACT

A method for labelling a tissue section is provided. In certain embodiments, the method may comprise: (a) labeling a formalin-fixed paraffin embedded (FFPE) tissue section using a first set of labeling reagents that comprises a first primary antibody and a first labeled secondary antibody; (b) treating the labeled tissue with a protease, thereby digesting the first primary antibody and/or the first labeled secondary antibody and separating the label from the FFPE tissue section; (c) washing the tissue section to remove the separated label and the protease; and (c) labeling the FFPE tissue section using a second set of labeling reagents that comprises a second primary antibody and a second labeled secondary antibody. A kit for performing the method is also provided.

19 Claims, 5 Drawing Sheets

MULTIPLE EPITOPE DETECTION IN AN FFPE TISSUE SECTION

BACKGROUND

The use of chromogens as substrates to detect specific antigens is currently used by pathologists to diagnose biopsied tissue samples. The ability to detect multiple antigens in the same tissue section has the advantage of providing more validating data regarding the disease status of the patient. This can be critical especially when the amount of tissue is limited and multiple sections do not exist. Multiplexed detection allows one to study two or more antigens in the same cell; if the presence overlaps in space, this is known as co-localization. In order to detect this, two or more separate colors should be observed.

SUMMARY

A method for labelling a tissue section is provided. In certain embodiments, the method may comprise: (a) labeling a formalin-fixed paraffin embedded (FFPE) tissue section using a first set of labeling reagents that comprises a first primary antibody and a first labeled secondary antibody; (b) treating the labeled tissue with a protease, thereby digesting the first primary antibody and/or the first labeled secondary antibody and separating the label from the FFPE tissue section; (c) washing the tissue section to remove the separated fluorescent label and the protease; and (c) labeling the FFPE tissue section using a second set of labeling reagents that comprises a second primary antibody and a second labeled secondary antibody. A kit for performing the method is also provided.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
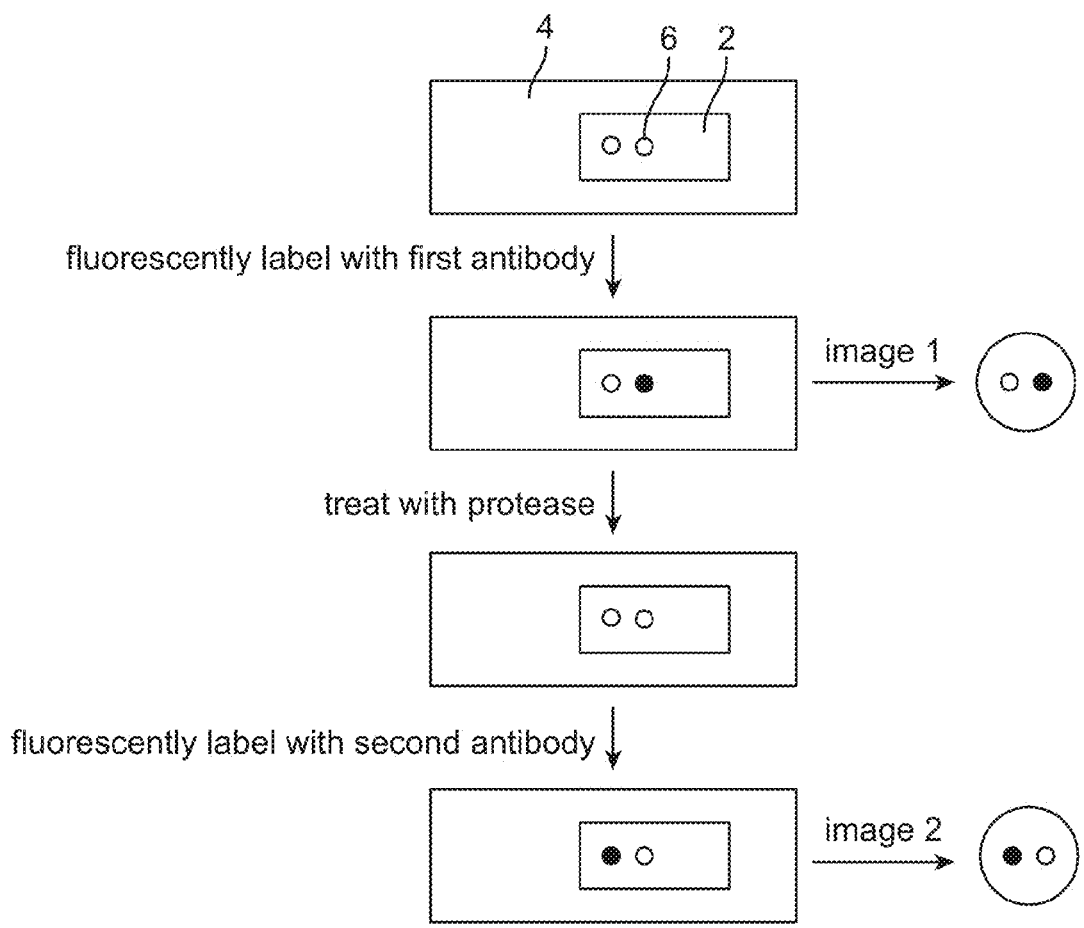
FIG. 1 schematically illustrates an overview of an embodiment of the present method.
Figure 2:
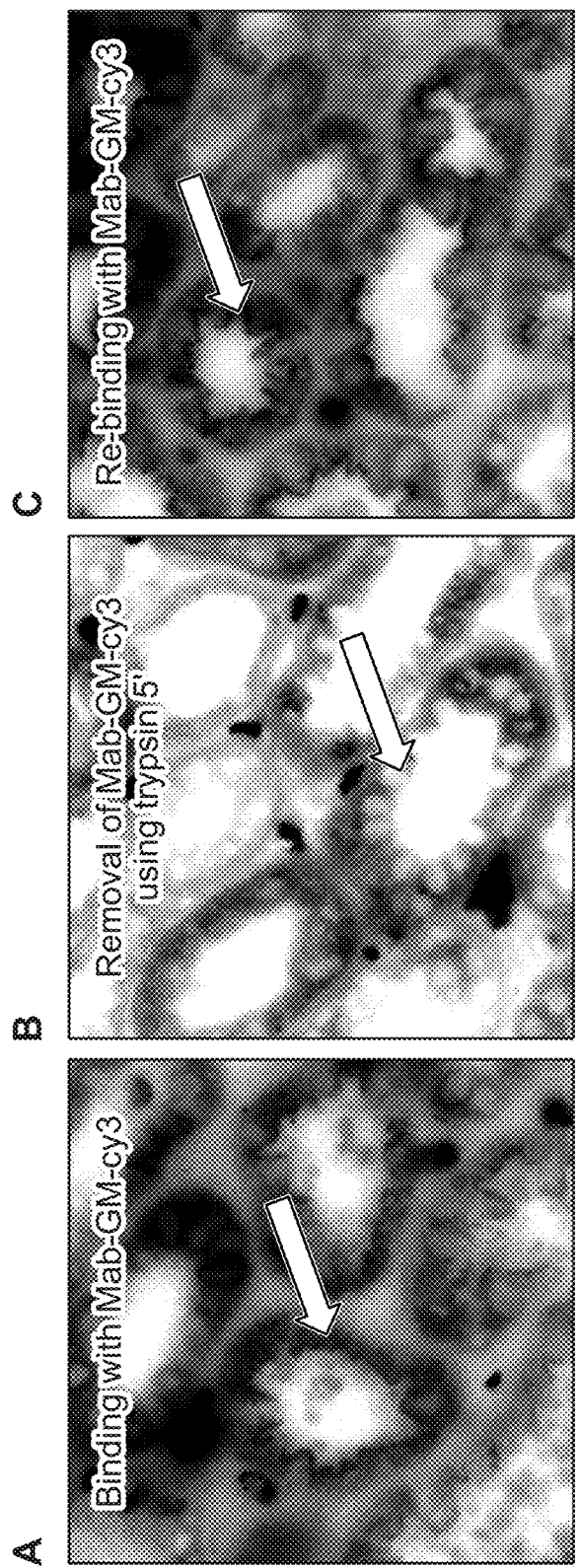
FIG. 2 shows binding of an anti-CA19-9 monoclonal antibody to a section of kidney. (A) Mab against CA19-9 was used in kidney. Note the positive staining in the luminal portion of the kidney tubules. (B) Incubation with 0.05% trypsin for 5 min at room temperature resulted in no restaining after incubating with the labeled secondary AB (Goat anti mouse IgG-cy3)(C) After trypsin removal, incubation with Mab to CA19-9 and the labeled antibody showed the ability to re-stain.
Figure 3:
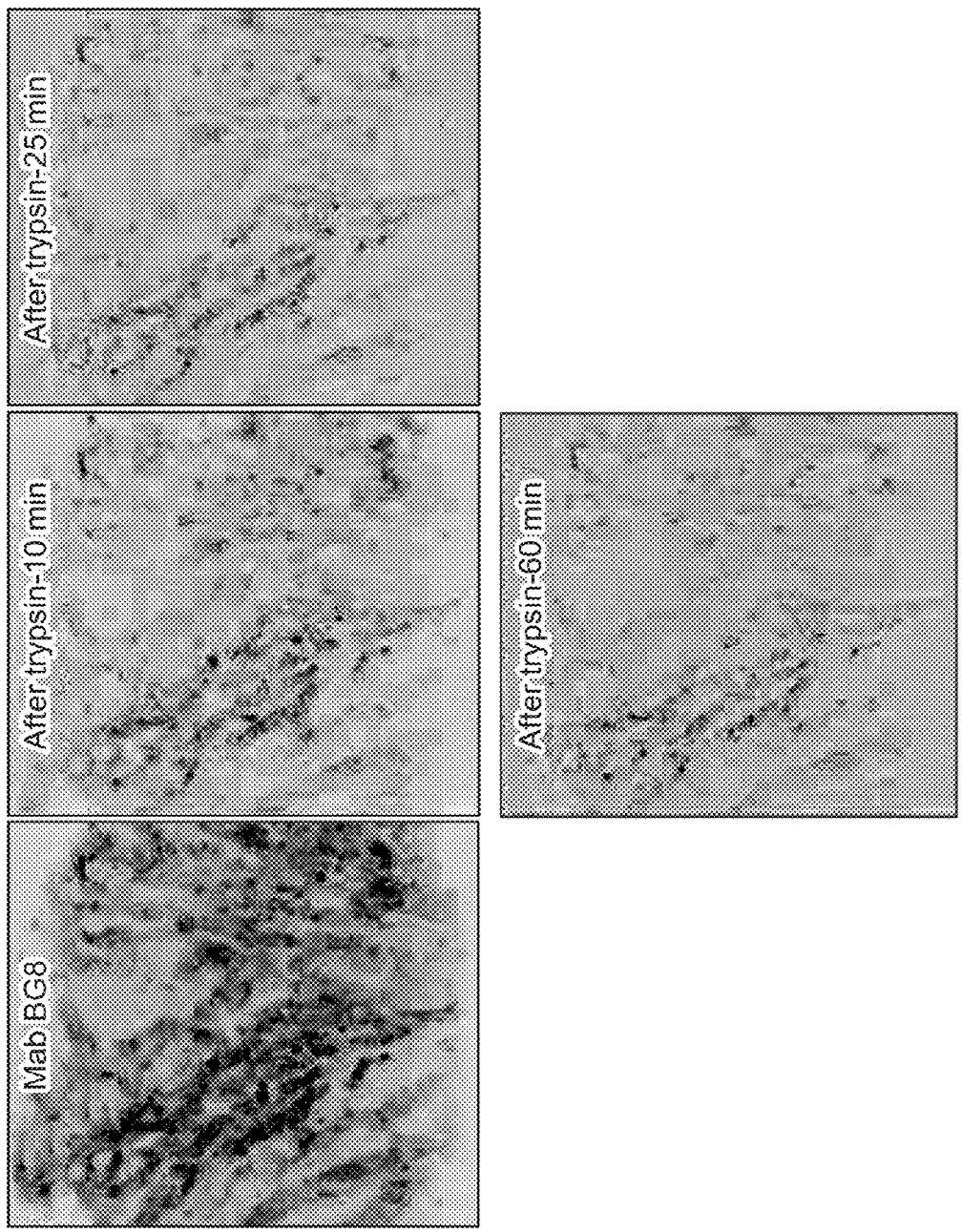
FIG. 3 shows binding of an anti-BG8 monoclonal antibody to a section of colon. In this experiment, 0.05% trypsin was incubated at the various times in colon tissue sections at room temperature. Optimal removal is observed at 25 min.
Figure 4:
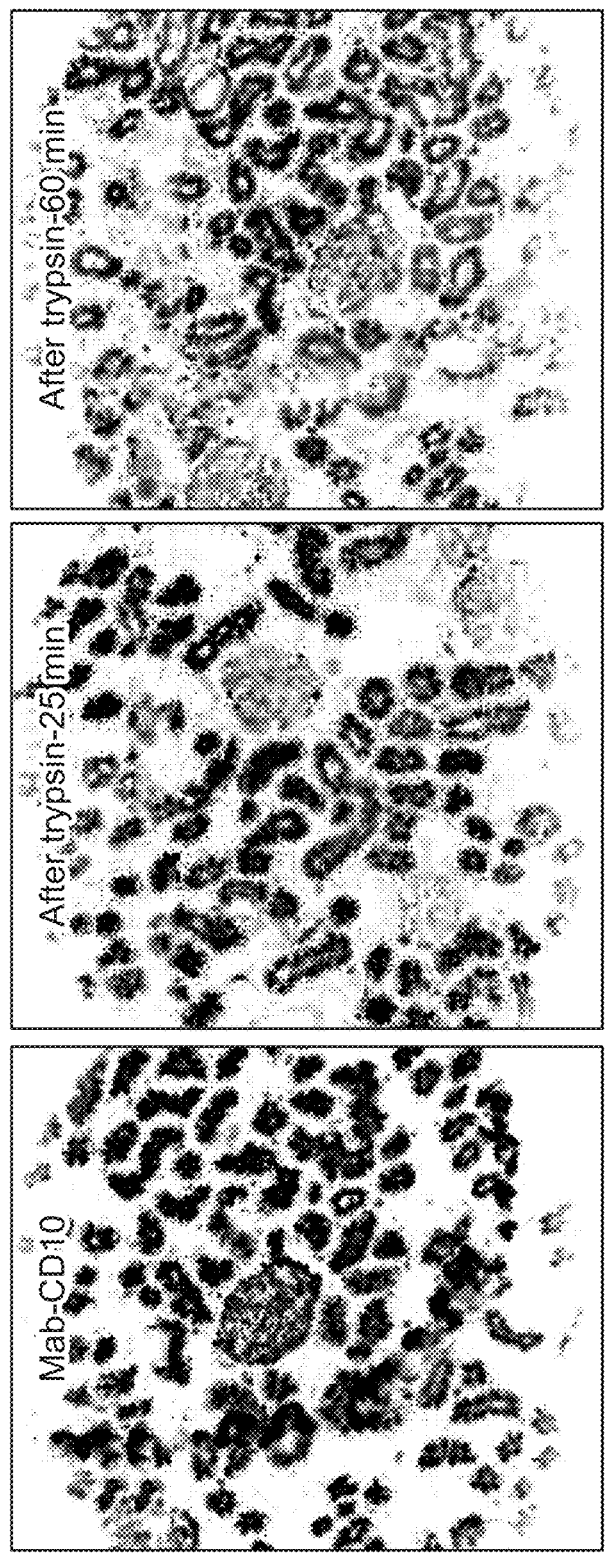
FIG. 4 shows binding of an anti-CD10 monoclonal antibody to a section of kidney. This is an example of using 0.05% trypsin for the times indicated above. CD-10 is highly expressed in kidney. The Mab dilution was 1:500 and the labeled secondary AB was 1:300. Trypsin removal may have been completed at 25 minutes if the Mab concentration and corresponding labeled secondary was used at a higher dilution but this was not tested.
Figure 5:
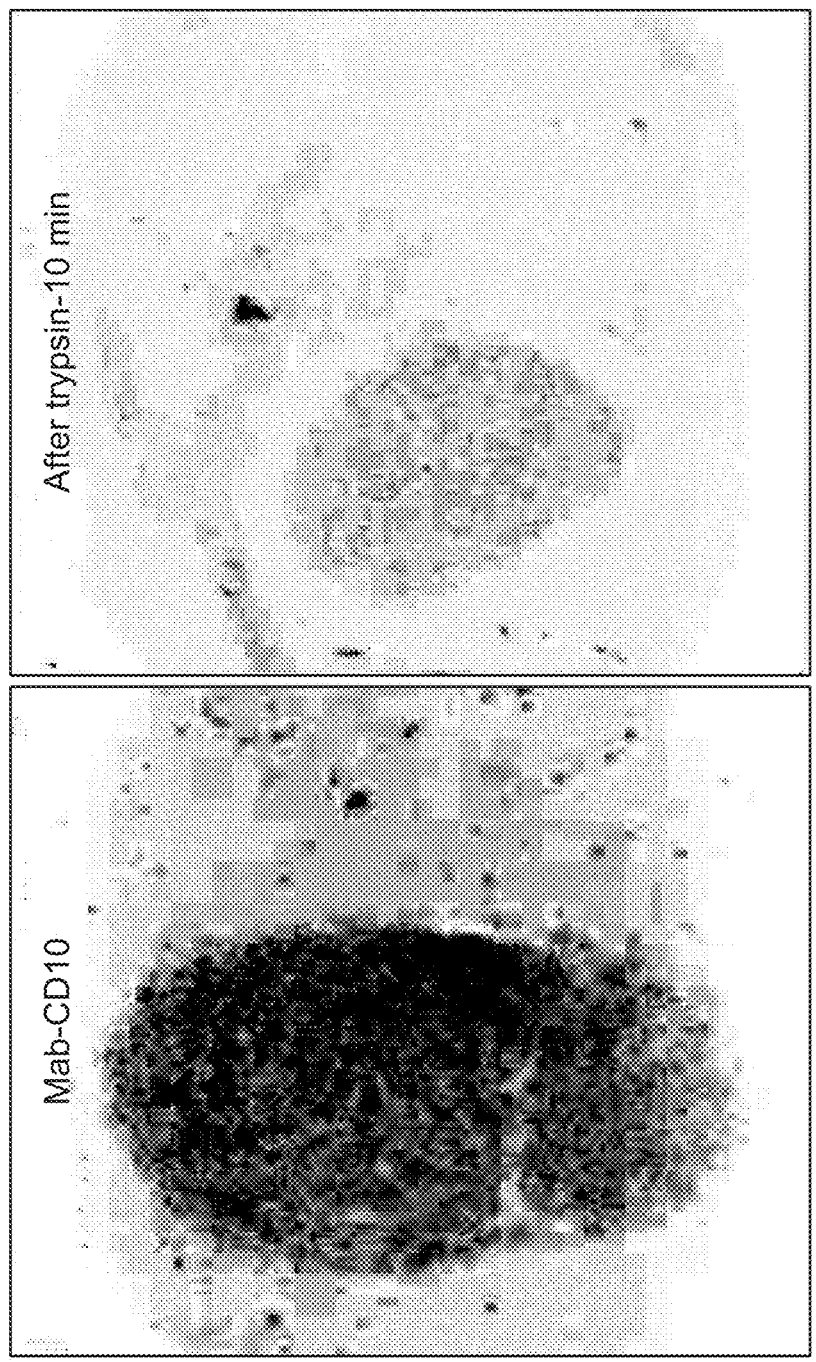
FIG. 5 shows binding of an anti-CD10 monoclonal antibody to a section of tonsil. Complete removal of Mab to CD-10 in tonsil sections using 0.05% trypsin for 10 min at room temperature.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

A "diagnostic marker" is a specific biochemical in the body which has a particular molecular feature that makes it useful for detecting a disease, measuring the progress of disease or the effects of treatment, or for measuring a process of interest.

A "pathoindicative" cell is a cell which, when present in a tissue, indicates that the animal in which the tissue is located (or from which the tissue was obtained) is afflicted with a disease or disorder. By way of example, the presence of one or more breast cells in a lung tissue of an animal is an indication that the animal is afflicted with metastatic breast cancer.

The term "epitope" as used herein is defined as small chemical groups on the antigen molecule that is bound to by an antibody. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

The term "labeling" includes first binding a sample to an unlabeled primary antibody that binds to an antigen, and then binding the unlabeled primary antibody with a secondary antibody that recognizes the primary antibody and is conjugated to a label. The label may be colorimetric, light emitting or fluorescent.

As used herein, the term "fluorescently labeling" refers to attaching a detectable fluorophore to specific sites in a sample (e.g., sites containing an epitope for the antibody being used)

such that the presence and/or abundance of the sites can be determined by evaluating the presence and/or abundance of the label.

As used herein, the term "multiplexing" refers to using more than one label for the simultaneous or sequential detection and measurement of biologically active material.

As used herein, the terms "antibody" and "immunoglobulin" are used interchangeably and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (e.g., $IgG_1$, $IgG_2$, $IgG_3$, and $IgG_4$), delta, epsilon and mu heavy chains or equivalents in different species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. Also encompassed by the term are Fab', Fv, F(ab')$_2$, and other antibody fragments that retain specific binding to antigen, and monoclonal antibodies. Antibodies may exist in a variety of other forms including, for example, Fv, Fab, and (Fab')$_2$, as well as bifunctional (i.e. bi-specific) hybrid antibodies (e.g., Lanzavecchia et al., Eur. J. Immunol. 17, 105-111 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

The term "specific binding" refers to the ability of a binding agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding agent and analyte when they are specifically bound in a capture agent/analyte complex is characterized by a $K_D$ (dissociation constant) of less than $10^{-6}$M, less than $10^{-7}$ M, less than $10^{-8}$ M, less than $10^{-9}$ M, less than $10^{-10}$ M, less than $10^{-11}$ M, or less than about $10^{-12}$ M or less.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a microscope slide.

As used herein, the term "treating" refers the act of combining one thing with another in a way that results in a reaction, e.g., proteolysis.

As used herein, the term "digesting" refers to a proteolytic cleavage reaction.

As used herein, the terms "primary antibody" and "secondary antibody" refer to different antibodies, where a primary antibody is a polyclonal or monoclonal antibody from one species (rabbit, mouse, goat, donkey, etc.) that specifically recognizes an antigen (e.g., a biomarker) in a sample (e.g., a human tissue sample) under study, and a secondary antibody is an antibody (usually polyclonal) from a different species that specifically recognizes the primary antibody, e.g., in its Fc region.

Other definitions of terms may appear throughout the specification.

DETAILED DESCRIPTION

In order to further illustrate the present invention, the following specific examples are given with the understanding that they are being offered to illustrate the present invention and should not be construed in any way as limiting its scope.

FIG. 1 illustrates some features of an embodiment of the present method. With reference to FIG. 1, one embodiment of the method comprises labeling a formalin-fixed paraffin embedded (FFPE) tissue section 2. As shown, tissue section 2 is mounted on glass slide 4. The labeling is done using a first set of labeling reagents that comprises a first primary antibody and a first labeled secondary antibody, i.e., a secondary antibody that is conjugated to a label, where the primary antibody binds to an antigen in the sample and the secondary antibody binds to the primary antibody and emits a signal that allows the binding event to be detected. As shown, the primary antibody binds to an antigen that is present in structure 6 (which could be a cell or subcellular component, for example). At this point, the tissue section can be optionally imaged using microscopy, e.g., a light microscope or fluorescent microscope, so that the structure 6, to which the primary antibody binds, can be analyzed. Next, the method comprises treating the tissue section with protease, which digests the antibody complex bound to the antigen (i.e., by digesting the primary antibody and/or the secondary antibody) and separates the label from the structures to which it was bound. The tissue section can then be washed to remove the separated label, the protease, and antibody fragments, from the tissue section. As shown in FIG. 1, the structure that contains antigen 6 is no longer labeled after this step. Next, the method may comprise labeling the tissue section using a second set of labeling reagents that comprises a second primary antibody and a second labeled secondary antibody. Again, at this point, the tissue section can be optionally imaged so that structure 8, which contains the antigen to which the second primary antibody binds, can be analyzed. The images produced by the method may be viewed side-by-side or, in some embodiments, the images may be superimposed or combined. In some cases, the images may be in color, where the colors used in the images may correspond to the labels used. In certain embodiments, protease treatment and labeling steps may be repeated one or more, e.g., two, three or four or more times. The first primary antibody and the second primary antibody may be the same antibody, different antibodies that bind to the same epitope, different antibodies that bind to different epitopes on the same protein, or different antibodies that bind to different proteins.

The label may be (i) light emitting (e.g., chemiluminiscent), (ii) an enzyme that catalyzes a colorigenic reaction (e.g., alkaline phosphatase and horseradish peroxidase, which cleave DAB or BCIP/NBT to produce a brown or purple color), (iii) biotin (which can be detected by binding to a labeled a streptavidin or neutravidin protein, or, as will be described in greater detail below (iv) fluorescent.

In some embodiments, the labelling may be fluorescent. In these embodiments, the method may comprise fluorescently labeling an (FFPE) tissue section using a first set of labeling reagents that comprises a first primary antibody and a first fluorescently labeled secondary antibody, i.e., a secondary antibody that is conjugated to a fluorescent label, where the primary antibody binds to an antigen in the sample and the secondary antibody binds to the primary antibody and emits a signal that allows the binding event to be detected. After optional imaging, the method may comprises treating the tissue section with protease, which digests the antibody complex (i.e., by digesting the primary antibody and/or the secondary antibody) and separates the fluorescent label from the structures to which it was bound. The tissue section can then be washed to remove the separated fluorescent label and the protease. Next, the method may comprise fluorescently labeling the tissue section using a second set of labeling reagents that comprises a second primary antibody and a second fluorescently labeled secondary antibody. Again, at this point, the tissue section can be optionally imaged. The images produced by the method may be viewed side-by-side or, in some embodiments, the images may be superimposed or combined. In some cases, the images may be in color, where the colors used in the images may correspond to the wavelength of fluorescent emission from each of the labels used.

The protease used in the method may be any suitable protease, including a serine protease, a metallo-protease, and a cysteine protease. In some embodiments, the protease used may be selected from the group consisting of trypsin (from, e.g., bovine), chymotrypsin (from, e.g., bovine), endoproteinase Asp-N (from, e.g., *Pseudomonas fragi*), endoproteinase Arg-C (from, e.g., mouse submaxillary gland and *Clostridium histolyticum*), endoproteinase Glu-C (from, e.g., *Staphylococcus aureus*), endoproteinase Lys-C (from, e.g., *Lysobacter enzymogenes*), pepsin (from, e.g., porcine), thermolysin (from, e.g., *Bacillus thermoproteolyticus*), elastase, papain (from, e.g., *Carica papaya*), proteinase K (from, e.g., *Tritirachium album*), subtilisin (from, e.g., *Bacillus subtilis*), proteinase K, furin, and ficin.

In some embodiments, the protease treatment may be milder than one would use to digest a sample containing, in solution, 1 µg of the primary antibody used and 1 µg of the secondary antibody used to 50% completion in the same buffer (e.g., 0.05% $CaCl_2$ (w/v) pH 7.8). In some embodiments, the protease treatment is so mild that, under the same conditions as used in the treatment step, only up to 1%, up to 5%, up to 10% or up to 20% of the primary and secondary antibodies may be digested. In some cases, the treating step may be done using a solution of 0.05% (w/v) trypsin containing 0.05% $CaCl_2$ (w/v) pH 7.8, for 5 to 30, e.g., 15 to 25 minutes, at room temperature, or an equivalent thereof, where an "equivalent" may involve compensating for an increase or decrease in the amount of enzyme by decreasing or increasing the incubation time, or by varying the temperature of the treatment, for example. Other milder conditions include using other formulations, e.g., 15 g glycine, 10 ml Tween 20 and adjusting the pH to 2.2 and bringing the volume to 1 L with water.

The amount of protease used in the method is sufficient to proteolytically digest the first and/or second antibodies, while leaving the tissue section and other epitopes that are in the section structurally intact. Without wishing to be bound to any particular theory, it is thought that the crosslinking may protect the other epitopes on the tissue sample from digestion.

In some embodiments, the labeling reagents used in the first labeling step may comprise a first set of primary antibodies that each bind to a different antigen. For example, the first set of primary antibodies may comprise a first antibody that binds to a first antigen, a second antibody that binds to a second antigen, a third antibody that binds to a third antigen and, optionally a fourth antibody that binds to a fourth and/or further antibodies that bind to further antigens. In these embodiments, the first primary antibodies may be from different species (e.g., goat, rabbit, mouse, camel, chicken, donkey, etc.) and the corresponding secondary antibodies may be distinguishably labeled. In these embodiments, the presence of several antigens can be detected by binding to the second set of labeling reagents, where each antigen is associated with a different or the same fluorophore.

In some embodiments, the labeling reagents used in the second labeling step may comprise a second set of primary antibodies that each bind to a different antigen. For example, the second set of primary antibodies may comprise a first antibody that binds to a first antigen, a second antibody that binds to a second antigen, a third antibody that binds to a third antigen and, optionally a fourth antibody that binds to a fourth and/or further antibodies that bind to further antigens. In these embodiments, the second primary antibodies may be from different species (e.g., goat, rabbit, mouse, camel, chicken, donkey, etc.) and the corresponding secondary antibodies may be distinguishably labeled. In these embodiments, the presence of several antigens can be detected by binding to the second set of labeling reagents, where each antigen is associated with a different fluorophore.

In some embodiments, the antibodies used in the first labeling step and the different labeling step all recognize different antigens. However, in some embodiments, there may be some overlap in the antigens bound by the antibodies of the first labeling step and second labeling step. In certain cases, an antibody used in the second labeling step may bind to the same antigen but at a different epitope relative to an antibody used in the first labeling step. In certain cases at least two of the primary antibodies of the first and second labeling steps recognize different epitopes on the same protein. In certain cases at least two of the primary antibodies of the first and second labeling steps recognize different epitopes on different proteins.

As would be apparent, the fluorescently labeling steps may each be done by incubating the tissue section with the primary antibody and then, after the primary antibody has bound to the tissue section, incubating the tissue section with the labeled secondary antibody.

The tissue section may be a section of a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In certain embodiments, the first primary antibody and the second primary antibody are antibodies that specifically bind to biomarkers, including cancer biomarkers. Exemplary cancer biomarkers, include, but are not limited to carcinoembryonic antigen (for identification of adenocarcinomas), cytokeratins (for identification of carcinomas but may also be expressed in some sarcomas), CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumour identification), CD20 (for identification of B-cell lymphomas) and CD3 (for identification of T-cell lymphomas).

The secondary antibodies may be attached to any suitable fluorophore. In certain cases, a fluorophore may be a coumarin, a cyanine, a benzofuran, a quinoline, a quinazolinone, an indole, a benzazole, a borapolyazaindacene and or a xanthene including fluorescein, rhodamine and rhodol. In multiplexing embodiments, fluorophores may be chosen so that they are distinguishable, i.e., independently detectable, from one another, meaning that the labels can be independently detected and measured, even when the labels are mixed. In other words, the amounts of label present (e.g., the amount of fluorescence) for each of the labels are separately determinable, even when the labels are co-located (e.g., in the same tube or in the same area of the section).

Specific fluorescent dyes of interest include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g., Cy3, Cy5 and Cy7 dyes; coumarins, e.g., umbelliferone; benzimide dyes, e.g. Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, Napthofluorescein, Texas Red, Cy3, and Cy5, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 and TOPRO3 (Molecular Probes, Eugene, Oreg.). Further suitable distinguishable detectable labels may be found in Kricka et al. (Ann Clin Biochem. 39:114-29, 2002), Ried et al. (Proc. Natl. Acad. Sci. 1992: 89: 1388-1392) and Tanke et al. (Eur. J. Hum. Genet. 1999 7:2-11) and others.

Antibody binding can be viewed with a fluorescence microscope and an appropriate filter for each fluorophore, or by using dual or triple band-pass filter sets to observe multiple fluorophores. See, e.g., U.S. Pat. No. 5,776,688.

The above-described method can be used to analyze cells from a subject to determine, for example, whether the cell is normal or not or to determine whether the cells are responding to a treatment. In one embodiment, the method may be employed to determine the degree of dysplasia in cancer cells.

In these embodiments, the cells may be a sample from a multicellular organism. A biological sample may be isolated from an individual, e.g., from a soft tissue. In particular cases, the method may be used to distinguish different types of cancer cells in FFPE samples.

After the images have been obtained, the images may be overlaid and analyzed to identify the boundaries of individual cells, and/or subcellular features in individual cells, in the image. Computer-implemented methods for segmenting images of cells are known in the art and range from relatively simple thresholding techniques (see, e.g., Korde et al. Anal Quant Cytol Histol. 2009 31: 83-89 and Tuominen et al. Breast Cancer Res. 2010 12: R56), to more sophisticated methods, such as, for instance, adaptive attention windows defined by the maximum cell size (Ko et al. J Digit Imaging. 2009 22: 259-274) or gradient flow tracking (Li, et al. J Microsc. 2008 231: 47-58). Some suitable image segmentation methods may be reviewed in Ko et al. (J Digit Imaging. 2009 22: 259-74) and Ong et al. (Comput Biol Med. 1996 26:269-79). Next the data that corresponds to each of the individual cells, or a subcellular feature thereof, that have been defined by the segmenting are integrated to provide, for each cell, values that indicate which markers are associated with the cell. In certain cases, a cell may be identified as being pathoindicative as a result of this analysis. This data may allow one to potentially type the cells in the sample. As such, this method may comprise displaying an image of the sample, in which the cells are color-coded by their type.

The method described above allows one to detect multiple antigens in the same tissue section. The ability to remove the antibody and its secondary binding antibody conjugated to a fluorophore from the antigenic site allows for detection of any co-localized antigens in the same cell by using standard reagents that are readily available. The method does not require specialized reagents which can only be used with a particular fluorophore. This reaction itself can be multiplexed, as fluorescence detection of up to four fluorophores is easily accomplished using standard fluorescence microscopy. Therefore, the digestion, followed by another set of incubation, allows the number of markers that can be investigated to increase by 4n-fold, of which n=the number of times the digestive process is carried out. Using more sophisticated microscopy, it may be possible to increase from 4 fluorophore detection to many more, thereby allowing the multiplexing to be Xn where X=the number of fluorophores detected at once and n=the number of digestive cycles.

In alternative embodiments, the method described above can be practiced on tissue sections that have been fixed in other ways, including tissue sections that have been fixed in, e.g., acrolein, glyoxal, smium tetroxide, arbodiimide, mercuric chloride, zinc salts, picric acid, potassium dichromate, ethanol, methanol, acetone, and/or acetic acid.

In other embodiments, the method may be performed without using secondary antibodiess. In these methods, the primary antibodies are labeled. In these embodiments, the method may comprises: (a) labeling a formalin-fixed paraffin embedded (FFPE) tissue section using a first labeled primary antibody; (b) treating the labeled tissue with a protease, thereby digesting the first labeled primary antibody and separating the label from the FFPE tissue section; (c) washing the tissue section to remove the separated label and the protease; and (d) labeling the FFPE tissue section using a second labeled primary antibody.

For this method the tissue sections need to be treated for immunohistochemical staining using standard protocols and optimized as necessary for each primary antibody, using standard processes. Our invention may be commercialized as a reagent to be used between incubation with sets of antibodies.

The method described above finds particular utility in examining tissue sections using a plurality of antibodies, each antibody recognizing a different marker. Examples of cancers, and biomarkers that can be used to identify those cancers, are shown below. In these embodiments, one does not need to examine all of the markers listed below in order to make a diagnosis.

example, a remote location could be another location (e.g., office, lab, etc.) in the same city, another location in a different city, another location in a different state, another location in a different country, etc. As such, when one item is indicated as being "remote" from another, what is meant is that the two items can be in the same room but be separated, or at least in different rooms or different buildings, and can be at least one mile, ten miles, or at least one hundred miles apart. "Communicating" information references transmitting the data rep-

| Cancer | Markers |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel - Female) | CK7, CK20, mammaglobin, ER, TTF1, CEA, CA19-9, S100, synaptophysin, and WT-1. |
| Carcinoma Unknown Primary Site, Male (CUPS IHC Panel - Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma IHC Panel | CDX2, CK 20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. |

In some embodiments, the method may involve obtaining an image as described above (an electronic form of which may have been forwarded from a remote location) and may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location," where "remote location" means a location other than the location at which the image is examined. For resenting that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or include email transmissions and information recorded on websites and the like. In certain embodiments, the image may be analyzed by an MD or other qualified medical professional, and a report based on the results of the analysis of the image may be forwarded to the patient from which the sample was obtained.

Kits

Also provided by this disclosure are kits that contain reagents for performing immunofluorescence on an FFPE section, as described above. A kit may contain at least: (a) a first set of labeling reagents that comprises a first primary antibody and a first fluorescently labeled secondary antibody; (b) a protease; (c) a wash buffer; and (d) a second set of labeling reagents that comprises a second primary antibody and a second fluorescently labeled secondary antibody. In certain embodiments, the first set of labeling reagents comprises: a first set of primary antibodies that each binds to a different antigen and a corresponding set of secondary antibodies that are distinguishably labeled; and the second set of labeling reagents comprises: a second set of primary antibodies that each binds to a different antigen and a corresponding set of secondary antibodies that are distinguishably labeled.

The kit may optionally contain other components, for example: binding buffers, blocking reagents and wash buffers, etc. The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Embodiments

Provided herein is a method for labelling a tissue section, comprising: (a) labeling a formalin-fixed paraffin embedded (FFPE) tissue section using a first set of labeling reagents that comprises a first primary antibody and a first labeled secondary antibody; (b) treating the labeled tissue with a protease, thereby digesting the first primary antibody and/or the first labeled secondary antibody and separating the label from the FFPE tissue section; (c) washing the tissue section to remove the separated label and the protease; and (d) labeling the FFPE tissue section using a second set of labeling reagents that comprises a second primary antibody and a second labeled secondary antibody.

In some embodiments, the method comprises (a) fluorescently labeling a formalin-fixed paraffin embedded (FFPE) tissue section using a first set of labeling reagents that comprises a first primary antibody and a first fluorescently labeled secondary antibody; (b) treating the labeled tissue with a protease, thereby separating the fluorescent label from the FFPE tissue section; (c) washing the tissue section to remove the separated fluorescent label and the protease; and (d) fluorescently labeling the FFPE tissue section using a second set of labeling reagents that comprises a second primary antibody and a second fluorescently labeled secondary antibody.

In any embodiment, the method may comprise imaging the FFPE tissue sample between step (a) and step (b), and after step (c).

In any embodiment, the method may comprise viewing the images, side by side or superimposed.

In any embodiment, the imaging may be done by microscopy, e.g., fluorescence microscopy.

In any embodiment, the protease may be a serine protease.

In any embodiment, the protease may be trypsin.

In any embodiment, the tissue section may be a section of a biopsy obtained from a patient.

In any embodiment, the first primary antibody and the second primary antibody may be antibodies that specifically bind to cancer markers.

In any embodiment, the first set of labeling reagents may comprise a first set of primary antibodies that each binds to a different antigen and a corresponding set of secondary antibodies that are distinguishably labeled; and the second set of labeling reagents may comprise a second set of primary antibodies that each binds to a different antigen and a corresponding set of secondary antibodies that are distinguishably labeled.

In any embodiment, the secondary antibodies may be from goat, rabbit and/or mouse.

In any embodiment, the fluorescently labeling steps (a) and (d) may be done by: incubating the tissue section with the primary antibody and then, after the primary antibody has bound to the tissue section, incubating the tissue section with the secondary antibody, thereby fluorescently labeling the tissue sample.

In any embodiment, the primary antibodies may be polyclonal antibodies.

In any embodiment, the primary antibodies may be monoclonal antibodies.

In any embodiment, the primary antibodies may be rabbit or mouse monoclonal antibodies.

In any embodiment, at least two of the primary antibodies of steps (a) and (d) may recognize different epitopes on the same protein.

In any embodiment, at least two of the primary antibodies of steps (a) and (d) may recognize different epitopes on different proteins.

Also provided is kit for performing immunohistochemistry on an FFPE section, comprising: (a) a first set of labeling reagents that comprises a first primary antibody and a first labeled secondary antibody; (b) a protease; (c) a wash buffer; and (d) a second set of labeling reagents that comprises a second primary antibody and a second labeled secondary antibody. The kit may comprise instructions for performing the present method.

In any kit embodiment, the first set of labeling reagents may comprise a first set of primary antibodies that each binds to a different antigen and a corresponding set of secondary antibodies that are labeled with fluorophores that are distinguishable from one another; and the second set of labeling reagents may comprise: a second set of primary antibodies that each binds to a different antigen and a corresponding set of secondary antibodies that are labeled with fluorophores that are distinguishable from one another.

In order to further illustrate the present invention, the following specific examples are given with the understanding that they are being offered to illustrate the present invention and should not be construed in any way as limiting its scope.

Example 1

0.05% Trypsin, 0.05% $CaCl_s$ pH 7.8—room temperature

Material and Methods:

FFPE (Formalin fixed paraffin embedded tissue sections were de-paraffinized and antigen retrieval (97 C for 20 minutes in high pH (10-11) in Tris-HCl performed using a PT-100 instrument (DAKO, Denmark). The slides were washed for 5 min in wash buffer (DAKO Wash buffer) for 5 min.

The sections were then blocked with blocking solution (10% Normal Goat Serum (NGS), and 1% BSA) for 15 minutes to inhibit non-specific binding.

After a brief wash in wash buffer, the sections were incubated with primary antibodies directed against a number of antigens (CA19-9, CD-10, BG8) in a variety of tissue types (kidney, colon, tonsil, breast adenocarcinoma) and incubated for 1 hr. in a humidified chamber at room temperature.

The sections were washed for 5 min in wash buffer then incubated with the labeled (cy3) secondary antibody (Goat anti-Mouse IgG-cy3) for 1 hr at room temperature in a humidified chamber in the dark, to prevent bleaching.

After incubation, the sections were washed 5 min in wash buffer and allowed to semi-dry before applying a coverslip with DAPI stain (stain nuclei, blue) then viewed using a Nikon fluorescence microscope.

After confirming and controlling for specific antibody staining the slides were then immersed in PBS buffer for 5 min to remove the coverslip. After removing the coverslip, the sections were washed again in wash buffer for 5 min. A solution of 0.05% trypsin containing 0.05% $CaCl_2$ pH 7.8 was used to remove the primary-secondary antibody-cy3 complex from the tissue sections. Incubations varied from 5 min to one hour depending on the antigen and the expression level of the antigen (high, medium, low immunostaining).

Following trypsin incubation, tissue sections were washed 5 min in PBS and then wash buffer for 5 min.

To determine if the antibody and its secondary reporter antibody was completely removed, tissue sections were incubated again with the labelled secondary antibody for 1 hr in a humidified chamber.

Sections were washed for 5 min in wash buffer, then a coverslip was applied with DAPI stain and viewed with a fluorescence microscope.

To determine if restaining of the trypsinized slides with the primary antibody was possible, the tissue sections following trypsinization were blocked with 10% NGS and 1% BSA for 15 min, washed in wash buffer for 5 min, then incubated with the primary antibody for 1 hr in a humidified chamber at room temperature. This was followed by a 5 min wash in wash buffer and then incubation with the labeled (cy3) secondary antibody for 1 hr at room temperature in the dark. The tissue section was then washed in wash buffer and a coverslip was applied with DAPI stain and viewed with a fluorescence microscope.

Results:

Trypsin at 0.05% pH 7.8 was incubated with immunostained tissue sections for Kidney, colon, Breast adenocarcinoma and tonsil for CA19-9, CD-10 and BG8 antigens. Removal of the primary AB-2°—cy3 complex was achieved using a 5 min incubation. A time course study using trypsin at 5 min, 10 min, 25 min and 60 min indicates that removal can be achieved optimally at 25 min. Removal using trypsin should be done at room temperature only as heating at 37° C. resulted in compromising the morphology of the tissue sections after 15 minutes. Time of incubation at 0.05% trypsin concentration will depend on tissue type, antigen localization and dilution of the primary and labeled secondary antibodies. The dilution of the primary antibody and the labeled secondary antibody should be optimized to yield the best results without creating excess background and non-specific staining. These conditions will facilitate trypsin removal using the protocols described.

Trypsin removal using the protocol described resulted in the ability to restain with the same primary antibody-labeled secondary antibody for the specific antigen. This indicated that incubation in trypsin solution did not affect the antigenicity of the epitope for that specific antigen. In addition, the tissue sections could be incubated with another primary antibody-labeled secondary antibody against a different antigen resulting in localization of two antigens in the same FFPE tissue. These results are shown in FIGS. 2-5.

Example 2

Material and Methods

Different Concentrations of Trypsin and Times

Material and Methods:

FFPE tissue sections were deparaffinized and subjected to antigen retrieval. Slides were immunostained as described above.

Specifically CA19-9 antigen was immunostained and kidney sections were viewed. To remove the primary antibody and its labeled secondary antibody, different concentrations of trypsin (0.2%-0.025%) were used at two different incubation time points (15 minutes and 25 minutes) at room temperature. All incubations were performed in a humidified chamber. After incubation, sections were washed in PBS followed by washed in antibody diluent. To determine if removal of the primary antibody occurred, the tissue sections were stained with the secondary labeled antibody only for 1 hour. The same dilution of secondary labeled antibody was used for all conditions including the control (no trypsin).

Results:

Trypsin incubation for 15 min: From the 4 concentrations used (0.2%, 0.1%, 0.05% and 0.025%), only the 0.05% at 15 minutes yielded removal of the primary antibody-secondary-labeled AB complex without compromising the morphology. While all concentrations removed the primary antibody it was clear that higher or lower concentrations than 0.05% had some effect on the morphology of the tissue. It was observed that the appearance of the "dots" or vesicular like cytoplasmic components were present in tissues treated with 0.2%, 0.1% and 0.025%.

Trypsin incubation for 25 min: From the 4 concentrations used (0.2%, 0.1%, 0.05% and 0.025%) only the 0.05% trypsin and 0.025% trypsin for 25 minutes yielded removal of the primary antibody-secondary-labeled AB complex without compromising the morphology. It is unclear to me why the 0.025% trypsin incubated for 25 minutes did not have the vesicular dots that the 0.025% trypsin incubated for 15 min displayed.

Conclusions:

Based on this set of experiments, it appears that using 0.05% trypsin for 15 minutes and up to 25 minutes is effective at removing the primary AB-secondary labeled AB complex from immunostained FFPE tissues.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed is:

1. A method for labelling a tissue section, comprising:
   (a) labeling a formalin-fixed paraffin embedded (FFPE) tissue section using a first set of labeling reagents that comprises a first primary antibody and a first labeled secondary antibody;
   (b) treating the labeled tissue with a protease, thereby digesting the first primary antibody and/or the first labeled secondary antibody and separating the label from the FFPE tissue section;
   (c) washing the tissue section to remove the separated label and the protease; and
   (d) labeling the FFPE tissue section using a second set of labeling reagents that comprises a second primary antibody and a second labeled secondary antibody.

2. The method of claim 1, wherein the method comprises imaging the FFPE tissue sample between step (a) and step (b), and after step (c).

3. The method of claim 2, wherein the method comprises viewing the images, side by side or superimposed.

4. The method of claim 2, wherein the first and second labeled secondary antibodies are fluorescently labeled and the imaging is done by fluorescence microscopy.

5. The method of claim 1, wherein the protease is a serine protease.

6. The method of claim 1, wherein the protease is trypsin.

7. The method of claim 1, wherein the tissue section is a section of a biopsy obtained from a patient.

8. The method of claim 1, wherein the first primary antibody and the second primary antibody are antibodies that specifically bind to cancer markers.

9. The method of claim 1, wherein:
   the first set of labeling reagents comprises: a first set of primary antibodies that each binds to a different antigen and a corresponding set of secondary antibodies that are labeled with fluorophores that are distinguishable from one another; and
   the second set of labeling reagents comprises: a second set of primary antibodies that each binds to a different antigen and a corresponding set of secondary antibodies that are labeled with fluorophores that are distinguishable from one another.

10. The method of claim 9, wherein the secondary antibodies are from goat, rabbit, donkey and/or mouse.

11. The method of claim 1, wherein the labeling steps (a) and (d) are done by: incubating the tissue section with the primary antibody and then, after the primary antibody has bound to the tissue section, incubating the tissue section with the secondary antibody, thereby labeling the tissue sample.

12. The method of claim 1, wherein the primary antibodies are polyclonal antibodies.

13. The method of claim 1, wherein the primary antibodies are monoclonal antibodies.

14. The method of claim 12, wherein the primary antibodies are rabbit, or mouse monoclonal antibodies.

15. The method of claim 1, wherein at least one of the primary antibodies of steps (a) and (d) recognize different epitopes on the same protein.

16. The method of claim 1, wherein at least one of the primary antibodies of steps (a) and (d) recognize different epitopes on different proteins.

17. A kit for performing immunohistochemistry on an FFPE section, comprising:
   (a) a first set of labeling reagents that comprises a first primary antibody and a first labeled secondary antibody;
   (b) a protease;
   (c) a wash buffer; and
   (d) a second set of labeling reagents that comprises a second primary antibody and a second labeled secondary antibody.

18. The kit of claim 17, wherein the kit comprises instructions for performing the method of claim 1.

19. The kit of claim 17, wherein:
   the first set of labeling reagents comprises: a first set of primary antibodies that each binds to a different antigen and a corresponding set of secondary antibodies that are labeled with fluorophores that are distinguishable from one another; and
   the second set of labeling reagents comprises: a second set of primary antibodies that each binds to a different antigen and a corresponding set of secondary antibodies that are labeled with fluorophores that are distinguishable from one another.

* * * * *

UNITED STATES PATENT AND TRADEMARK OFFICE
CERTIFICATE OF CORRECTION

PATENT NO.         : 9,234,892 B2                               Page 1 of 1
APPLICATION NO.    : 14/273320
DATED              : January 12, 2016
INVENTOR(S)        : May Tom-Moy et al.

It is certified that error appears in the above-identified patent and that said Letters Patent is hereby corrected as shown below:

In the Specification

In column 3, line 48, delete "(1986))." and insert -- (1986). --, therefor.

In column 5, line 4-5, delete "chemiluminiscent)," and insert -- chemiluminescent), --, therefor.

In column 7, line 16, delete "and or" and insert -- and/or --, therefor.

In column 7, line 36, delete "benzimide" and insert -- benzamide --, therefor.

In column 7, line 44-45, delete "Napthofluorescein," and insert -- Naphthofluorescein, --, therefor.

In column 8, line 51, delete "smium" and insert -- osmium --, therefor.

In column 8, line 51, delete "arbodiimide," and insert -- carbodiimide, --, therefor.

In column 8, line 55, delete "antibodiess." and insert -- antibodies. --, therefor.

Signed and Sealed this
Twelfth Day of July, 2016

Michelle K. Lee
*Director of the United States Patent and Trademark Office*